US006319662B1

(12) United States Patent
Foley et al.

(10) Patent No.: US 6,319,662 B1
(45) Date of Patent: Nov. 20, 2001

(54) METHOD AND APPARATUS FOR REMOVING VIRAL CONTAMINANTS FROM A BODY FLUID

(75) Inventors: Jack Foley, Wheeling; John Chapman, Lake Villa; Ludwig Wolf, Jr., Inverness, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/168,438

(22) Filed: Dec. 17, 1993

(51) Int. Cl.⁷ .................................................... A01N 1/02
(52) U.S. Cl. .................................................. 435/2; 424/90
(58) Field of Search ................. 435/2; 424/89, 424/90, 529; 210/645, 650, 651, 654, 656, 660, 679, 692; 604/4, 5, 6, 252

(56) References Cited

U.S. PATENT DOCUMENTS

| 3,765,536 | 10/1973 | Rosenberg | 210/446 |
|---|---|---|---|
| 4,190,542 | 2/1980 | Hodgson | 210/282 |
| 4,728,432 | 3/1988 | Sugiyama | 210/646 |
| 4,748,120 | * 5/1988 | Wiesehahn | 435/173 |
| 4,878,891 | 11/1989 | Judy | 604/5 |
| 5,294,699 | 3/1994 | Ohmura | 530/364 |

FOREIGN PATENT DOCUMENTS

B-63391/90 * 3/1993 (AU) .
WO 91/03933 * 4/1991 (DE) .
A-124363   7/1984 (EP) .
A-366946   9/1990 (EP) .
WO-A-91-03933  4/1991 (WO) .
WO-A-95-00631  1/1995 (WO) .

OTHER PUBLICATIONS

Heinmets F., Inactivation of Viruses in Plasma by Photosensitized Oxidation WRAIR–53–55 Walter Reed Research Report 1955, pp. 1–16.*
Gusmari V., The Fractionation and Desalting of Serum . . . Bul I Shkeencave Mjeresore I 1981 pp. 75–80.
Badylak J., Photodynamic Inactivation of Pseudorabies . . . J of Clin Micro vol. 17 (2) 1983 pp. 374–376.
Biorad Catalog, Life Science Research Products 1993 pp. 11–12

* cited by examiner

*Primary Examiner*—Ralph Gitomer
(74) *Attorney, Agent, or Firm*—Robert M. Barrett; Bradford R. L. Price; Michael C. Mayo (57) ABSTRACT

A method for treating a body fluid to at least substantially inactivate viral contaminants that may be present therein is provided. The method includes the steps of: providing a body fluid; adding to the body fluid a viral inactivating agent to create a resultant product; and passing the resultant product through a column including material having an affinity for the viral inactivating agent.

1 Claim, 9 Drawing Sheets

METHOD AND APPARATUS FOR REMOVING VIRAL CONTAMINANTS FROM A BODY FLUID

BACKGROUND OF THE INVENTION

The present invention relates generally to the collection and therapeutic use of body fluids. More specifically, the present invention relates to methods and devices for attempting to substantially reduce or eliminate potential viral contaminants and other pathogens in body fluids, such as blood.

Of course, in a wide variety of therapies, such as transfusions and transplants, body fluids, especially blood components, such as red blood cells, platelets, plasma, and bone marrow, are infused from one or more individuals into a patient. Although such therapies provide treatments, many of which are life saving, and cannot otherwise be provided, due to the transmission of infectious diseases, there may be potential risks to such therapies.

For example, it is known that blood can carry infectious agents, such as hepatitis virus, human immune deficiency virus (an etiological agent for AIDS), cytomegalovirus, Epstein Barr virus, and herpes virus. Although screening methods exist to identify blood that may include such viruses, current screening methods do not assure that every blood unit that contains such a virus is identified.

For example, in this regard, one of the difficulties in testing blood components for viral contamination, such as HIV, is that many current diagnostic tests are based on an identification of antibodies. Therefore, a contaminated blood component will only exhibit a positive test if it includes antibodies for the virus, e.g., anti-HIV. With respect to intracellular viral infections, an individual may not generate antibodies immediately upon infection. Rather, there is a window period that extends from the initial infection of the patient with a virus to the generation of antibodies. When an individual is in this window period, diagnostic tests that are based on antibodies will not identify the individual, or the blood unit, as being infected. But, even though the antibodies are not present, the blood unit can still transmit an infection.

With respect to HIV infection, it is believed that this window period can extend from approximately six weeks up to 48 months. During this time period, an individual who has been infected with HIV and accordingly, whose blood will transmit same, will register a negative antibody response. Currently used screening methods will not identify as contaminated a blood unit from an individual who is infected with HIV, but who has not generated anti-HIV.

In order to address the limitations of current diagnostic techniques and also to deal with the concern of transmission of viral contaminants and other pathogens to a patient receiving a transfusion, recent attention has focussed on the development of viral inactivating agents. It is envisioned that these viral inactivation agents would be added to the body fluid prior to the body fluid being administered to the patient.

For example, a number of photoactive agents that have antiviral action have been explored. These photoactive agents are generally agents that upon activation with light will inactivate or destroy pathogens, e.g., a virus that may be present. Such photoactive agents include: psoralens; porphyrins; phthalocyanines; and dyes, such as methylene blue. See, for example, U.S. Pat. Nos.: 4,748,120; 4,878,891; 5,120,649; and German Patent Application No. DE 39 30 510 A1 (Mohr).

Although such agents provide promise for the treatment of body fluids to eliminate the concern of viral contamination, there may be regulatory, as well as possible other concerns with respect to such agents. Of course, the resultant body fluid to which the anti-viral agent is added will be infused into a patient. Therefore, it is imperative that the agent does not create toxicity issues or other in vivo concerns.

With respect to photoactive agents, a still further issue is that upon activation of the agent and interaction of the agent with a virus, other products may be generated. For example, methylene blue is a photoactive agent that has been shown to have efficacy in inactivating viral contamination in plasma. Although methylene blue has been, through exhaustive testing, shown to have no toxicity concerns, upon photoactivation of methylene blue, photoproducts are generated. Specifically, Azure A and B are generated upon photoactivation of methylene blue. The in vivo effect of these products has not been as well studied as methylene blue in patients and therefore they raise regulatory issues and in vivo concerns.

There therefore is a need for an improved method and system for treating a body fluid to substantially reduce, if not eliminate, viral contaminants that may be present therein.

SUMMARY OF THE INVENTION

The present invention provides a method of treating a body fluid to substantially inactivate viral contaminants that may be present therein. Pursuant to the method, to a body fluid is added a viral inactivation agent. The resultant product is then passed through a container, e.g., column including a material having an affinity for the viral inactivating agent. This allows the column to remove excess viral inactivating agent. Additionally, other products, e.g. photoproducts, that may be generated upon addition of the viral inactivation agent or any activation thereof are also eliminated. The body fluid can then be infused into a patient without regulatory or toxicity concerns.

To this end, in an embodiment, the present invention provides a method for treating a body fluid to at least substantially inactivate viral contaminants that may be present comprising the steps of: providing a body fluid; adding to the body fluid a viral inactivating agent to create a resultant product; and passing the resultant product through a column including material having an affinity for the viral inactivating agent.

In an embodiment, the material includes charcoal.

In an embodiment, the column is an ion exchange column.

In an embodiment, the material includes neural macroporous polymeric beads with a high surface area for absorbing organics from aqueous solutions.

In an embodiment, the viral inactivating agent is a light activated agent.

In an embodiment, the viral inactivating agent is chosen from the group consisting of: porphyrins; psoralens; phthalocyanines; and dyes.

The present invention also provides a method for treating a blood product comprising the steps of: providing a blood product; adding to the blood product a light activated viral inactivating agent to create a resultant product; irradiating the resultant product with light of a sufficient wavelength to activate the viral inactivating agent to create a further product; passing the further product through a column having an affinity for the viral inactivating agent; and collecting a product that passes through the column.

In an embodiment, the blood product includes platelets and the viral inactivating agent is a psoralen.

In an embodiment, the blood product includes plasma and the viral inactivating agent includes methylene blue.

In an embodiment, the column also has an affinity for photoproducts generated by irradiating the resultant product.

The present invention also provides a method for providing a blood product to a patient comprising the steps of: collecting a blood product from a donor; adding to the blood product a light activated viral inactivation agent; irradiating the blood product and light activated viral inactivation agent with light of a sufficient wavelength to activate the viral inactivation agent to create a resultant product; passing the resultant product through a column having an affinity for the viral inactivation agent; collecting a resultant blood product that passes through the column; and administering the resultant blood product to a patient.

An advantage of the present invention is that it provides an improved method for treating a body fluid to at least substantially inactivate viral contaminants that may be therein.

Another advantage of the present invention is that it provides a method for inactivating or eliminating pathogens from blood or its components before they are infused into a patient.

Furthermore, an advantage of the present invention is that it provides a system that allows viral inactivating agents to be added to a body fluid before the fluid is infused into a patient and eliminate toxicity or regulatory concerns.

Still further, an advantage of the present invention is that it provides a method for eliminating photoproducts from a system that adds a photoactive agent to a body fluid.

Moreover, an advantage of the present invention is that it prevents any post thaw photoactivation of excess photoactivated agents.

Another advantage of the present invention is that it allows normal plasma color for treated plasma.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a method and apparatus for use in treating a body fluid, such as blood, to reduce or eliminate viral contaminations that may be present therein. It is believed that the present invention can be used with a variety of viral inactivating agents. Such agents include, without limitation, photoinactivation agents, such as psoralens, porphyrins, dyes, such as methylene blue, phthalocyanines, phenothiazines, hypericin, and other compounds that are activated by light.

As has been suggested in the art, a photoactive viral inactivating agent would be added to a body fluid, such as blood prior to the blood being infused into a patient. The resultant blood product including the photoactive agent then would be activated by light of a suitable wavelength. Of course, if desired, other viral inactivating agents that are not based on activation through light can be utilized in the present invention.

Figure 1:
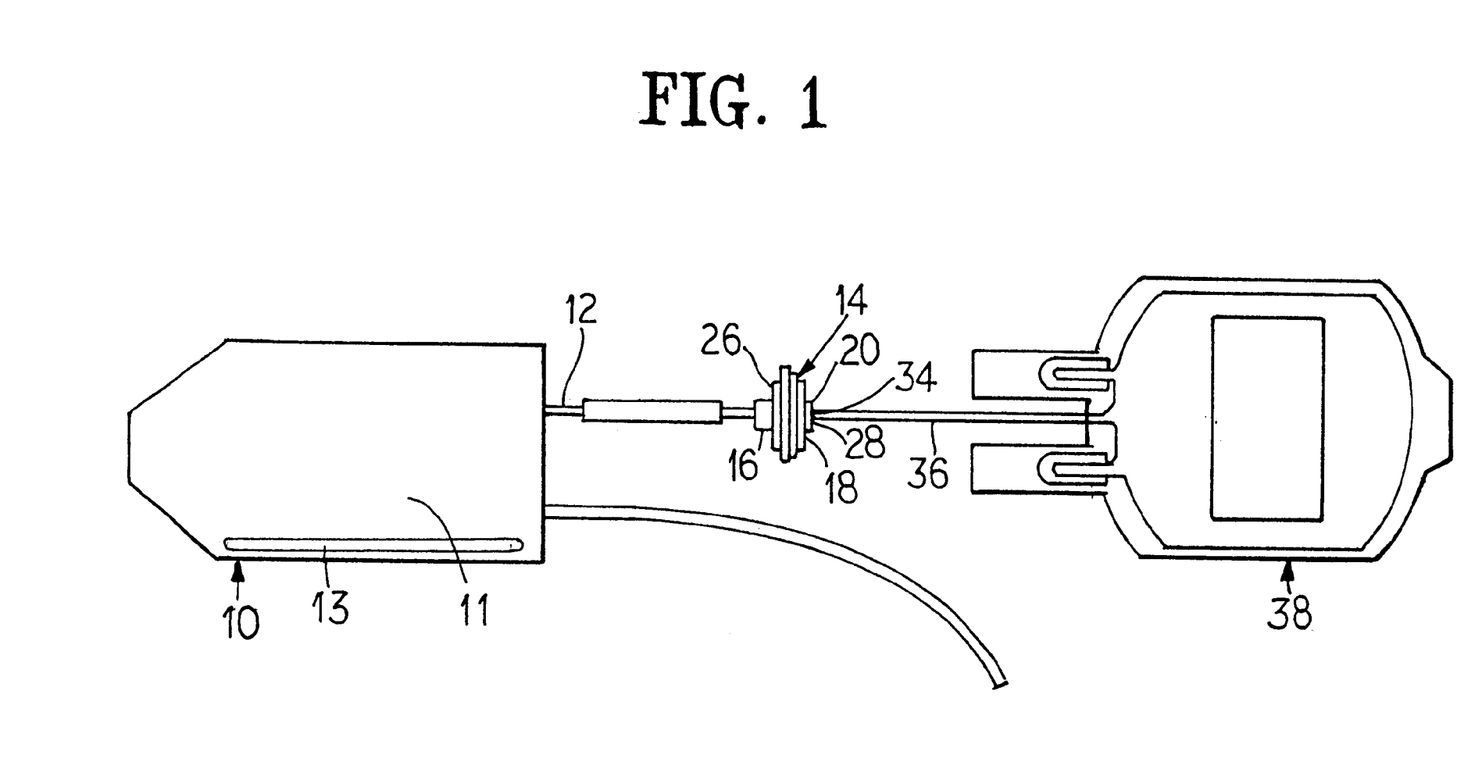
FIG. 1 illustrates, schematically, an embodiment of the system of the present invention.
Figure 2:
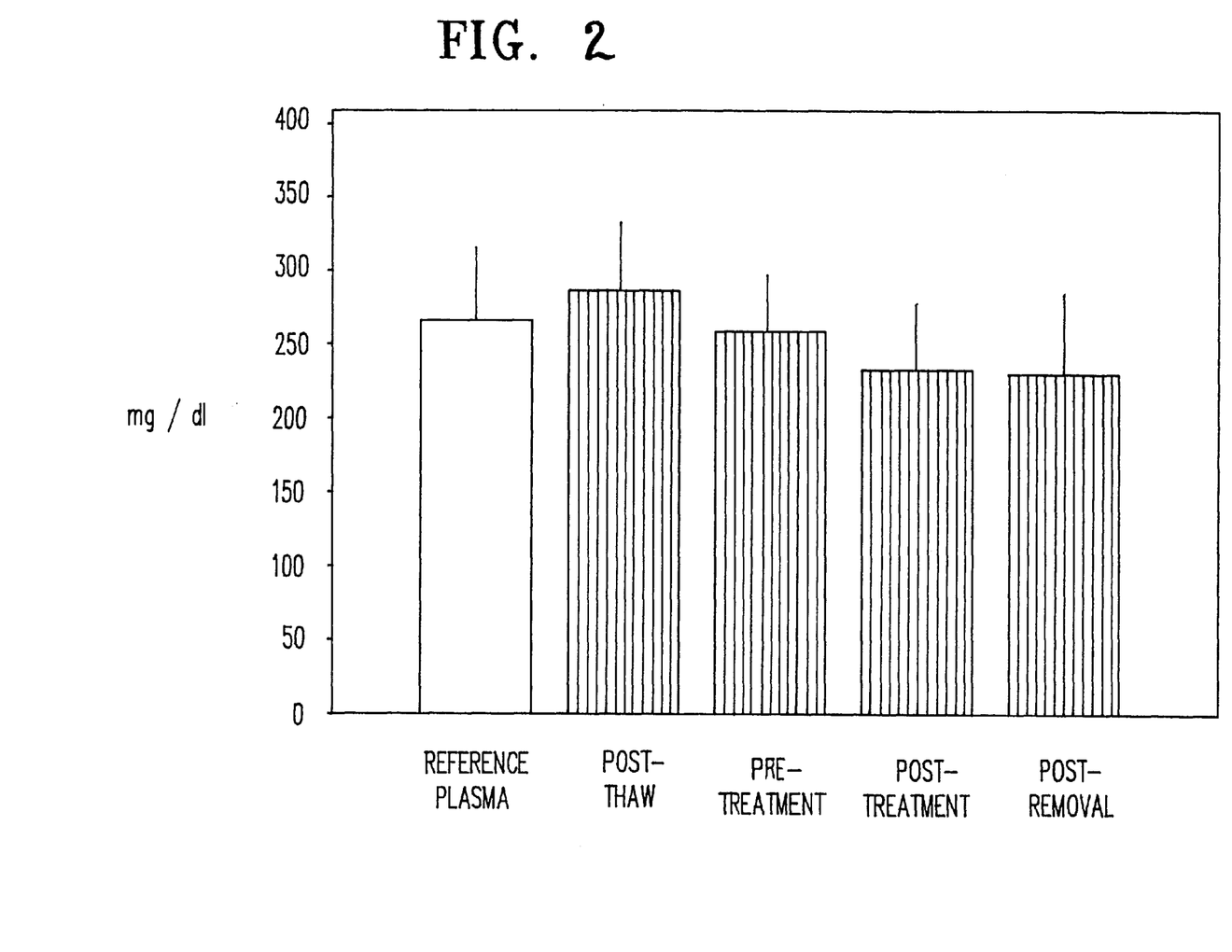
FIG. 2 illustrates graphically results of Example No. 3 and specifically, the content of fibrinogen in reference plasma, post-thaw, pretreatment, post treatment, and post removal.
Figure 3:
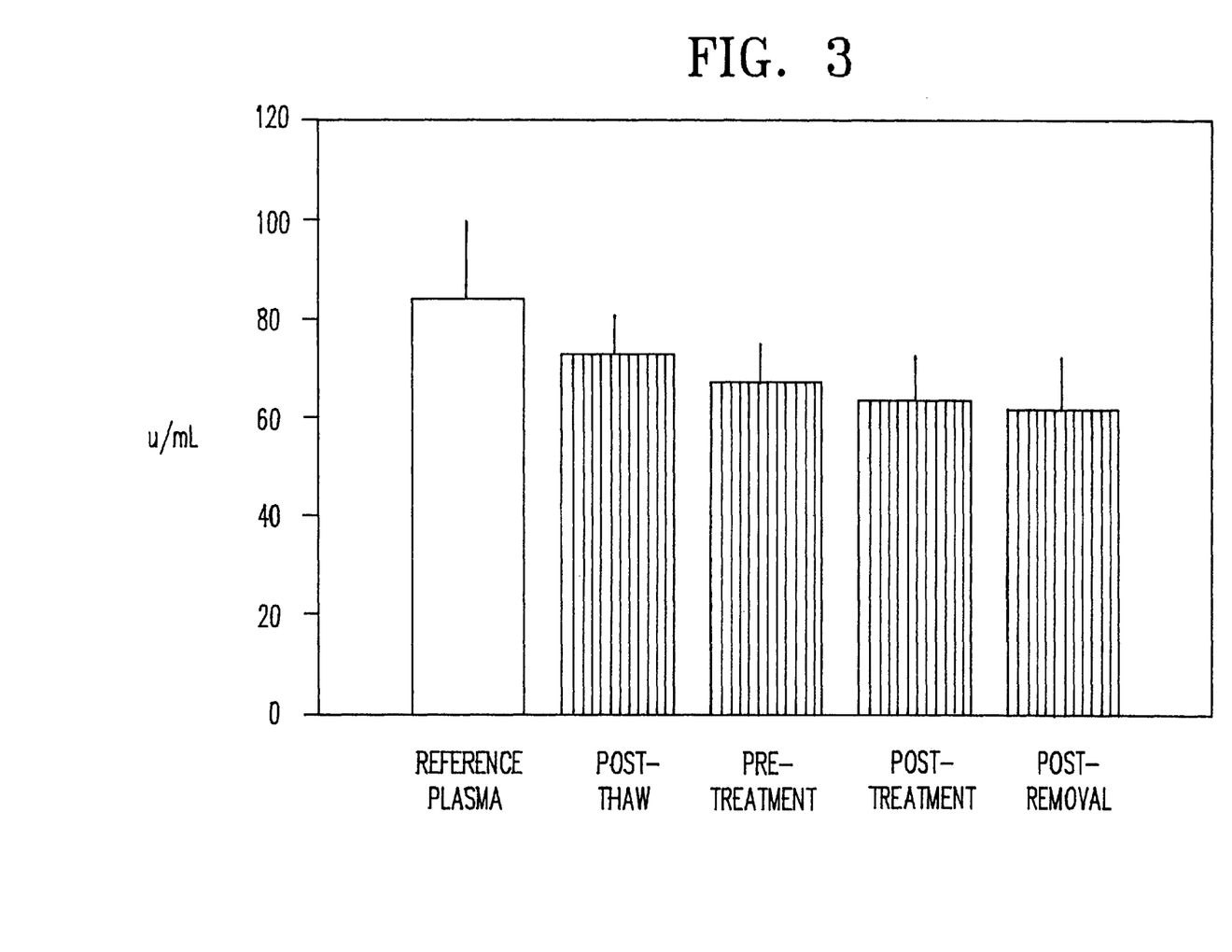
FIG. 3 illustrates graphically results of Example No. 3 and specifically, the content of Factor V in reference plasma, post-thaw, pretreatment, post treatment, and post removal.
Figure 4:
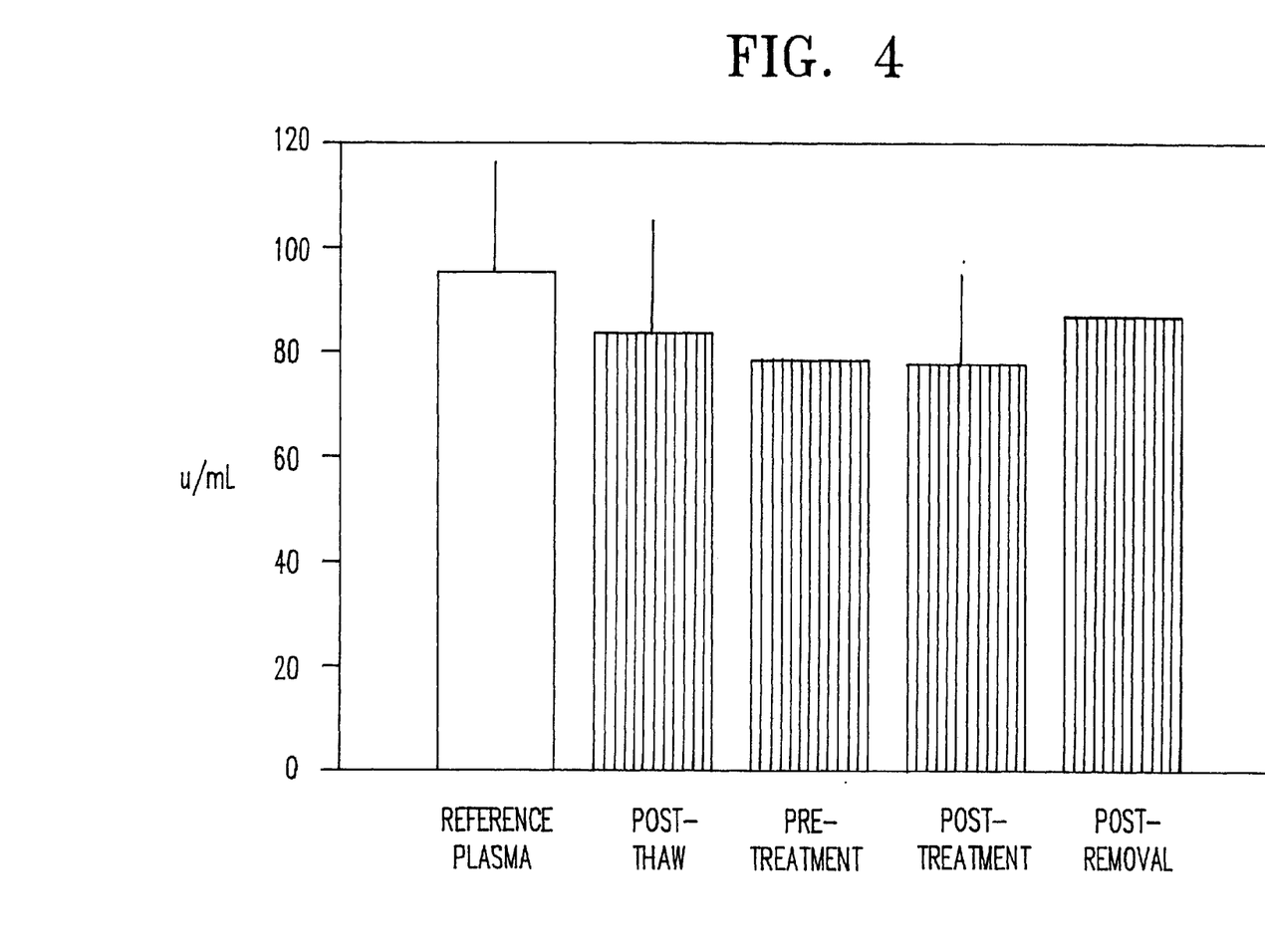
FIG. 4 illustrates graphically results of Example No. 3 and specifically, the content of Factor VII in reference plasma, post-thaw, pretreatment, post treatment, and post removal.
Figure 5:
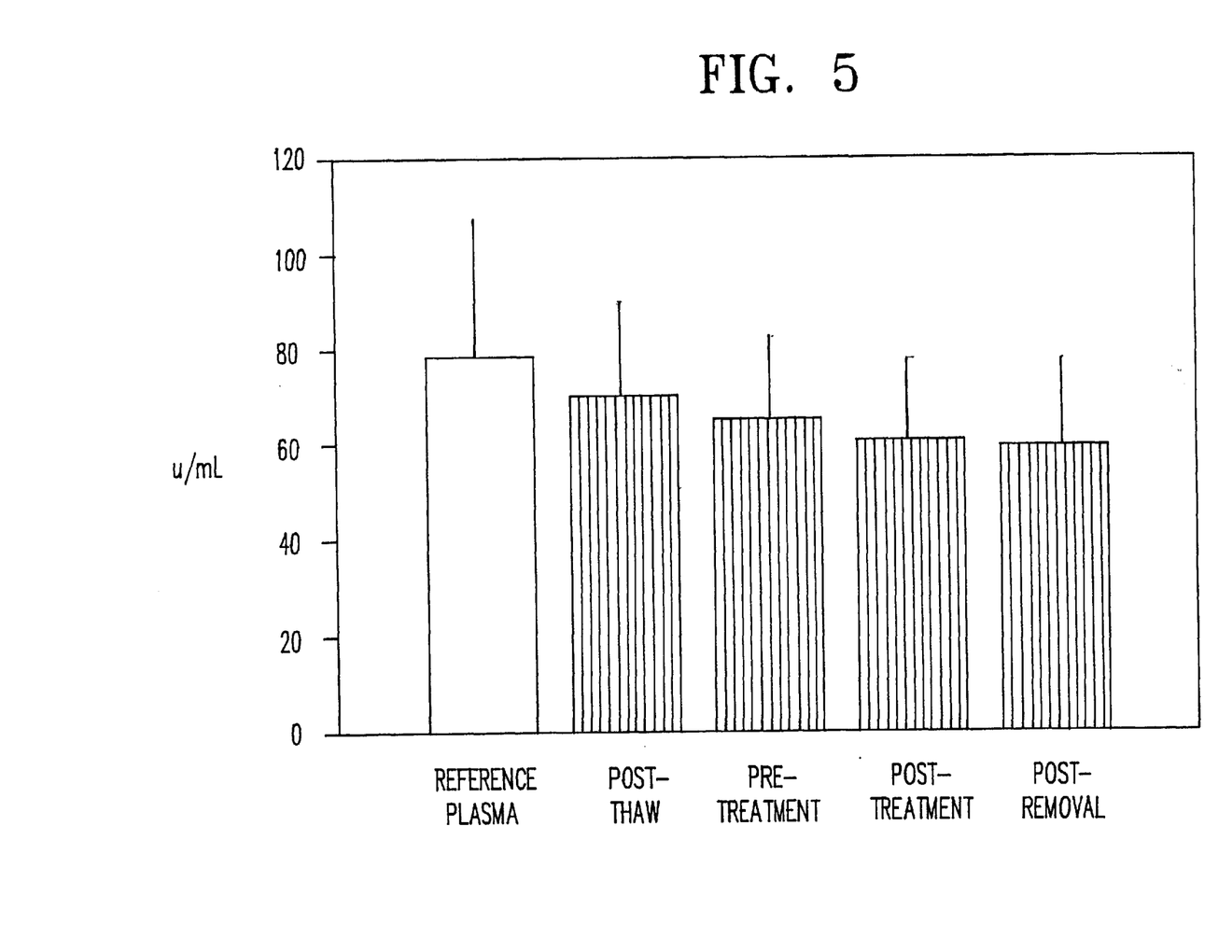
FIG. 5 illustrates graphically results of Example No. 3 and specifically, the content of Factor VIII:C in reference plasma, post-thaw, pretreatment, post treatment, and post removal.
Figure 6:
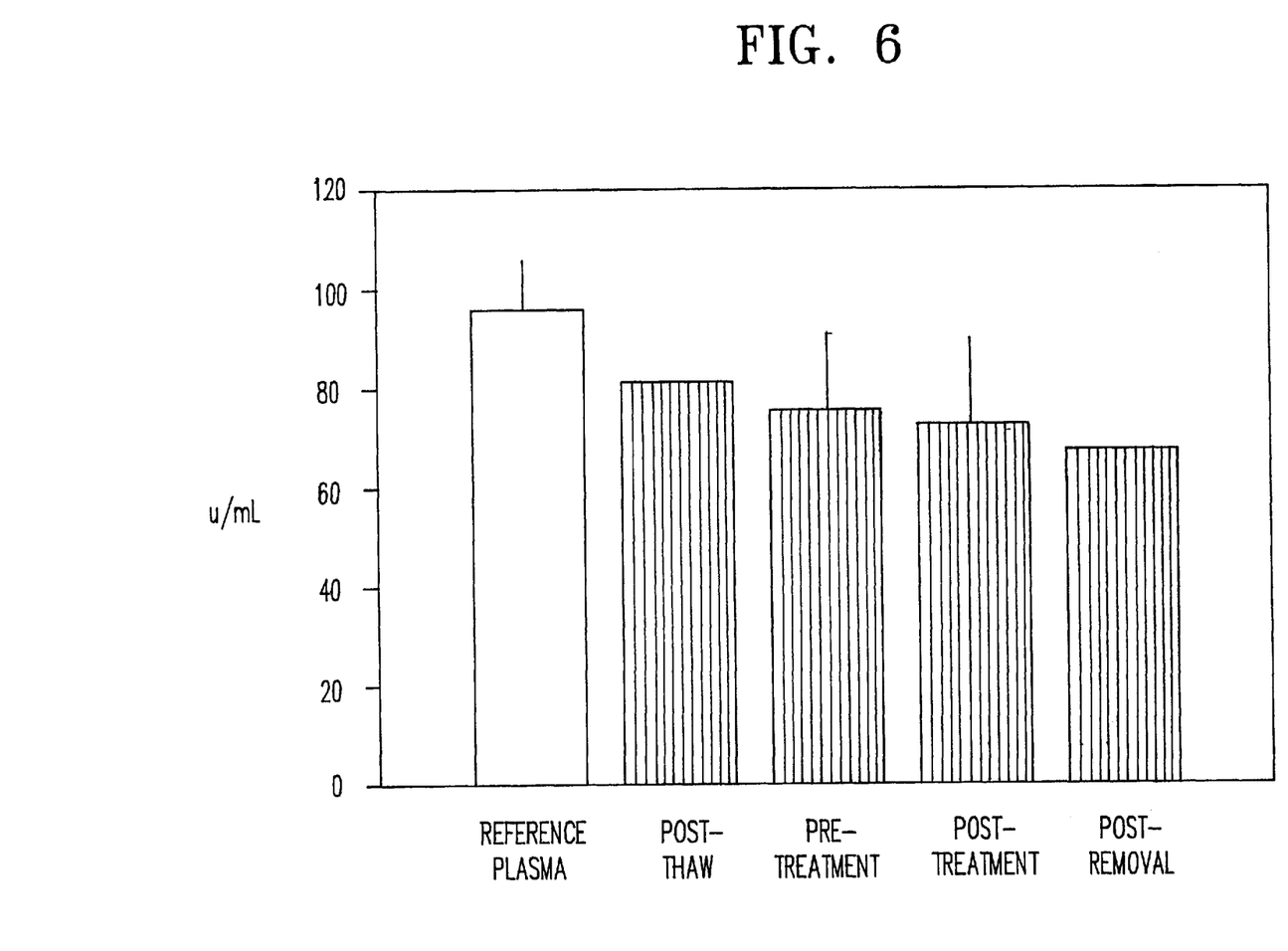
FIG. 6 illustrates graphically results of Example No. 3 and specifically, the content of Factor IX in reference plasma, post-thaw, pretreatment, post treatment, and post removal.
Figure 7:
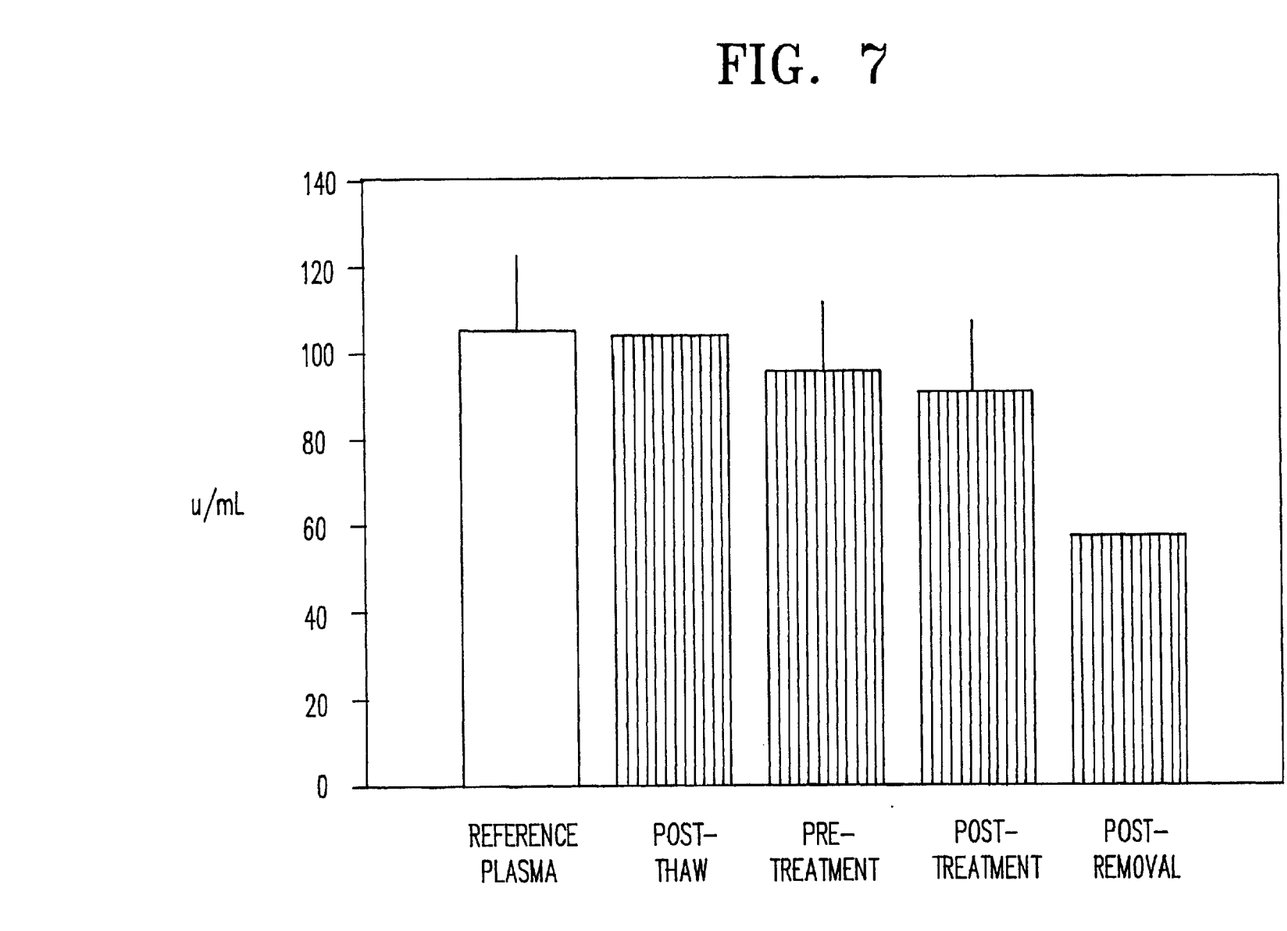
FIG. 7 illustrates graphically results of Example No. 3 and specifically, the content of Factor XI in reference plasma, post-thaw, pretreatment, post treatment, and post removal.
Figure 8:
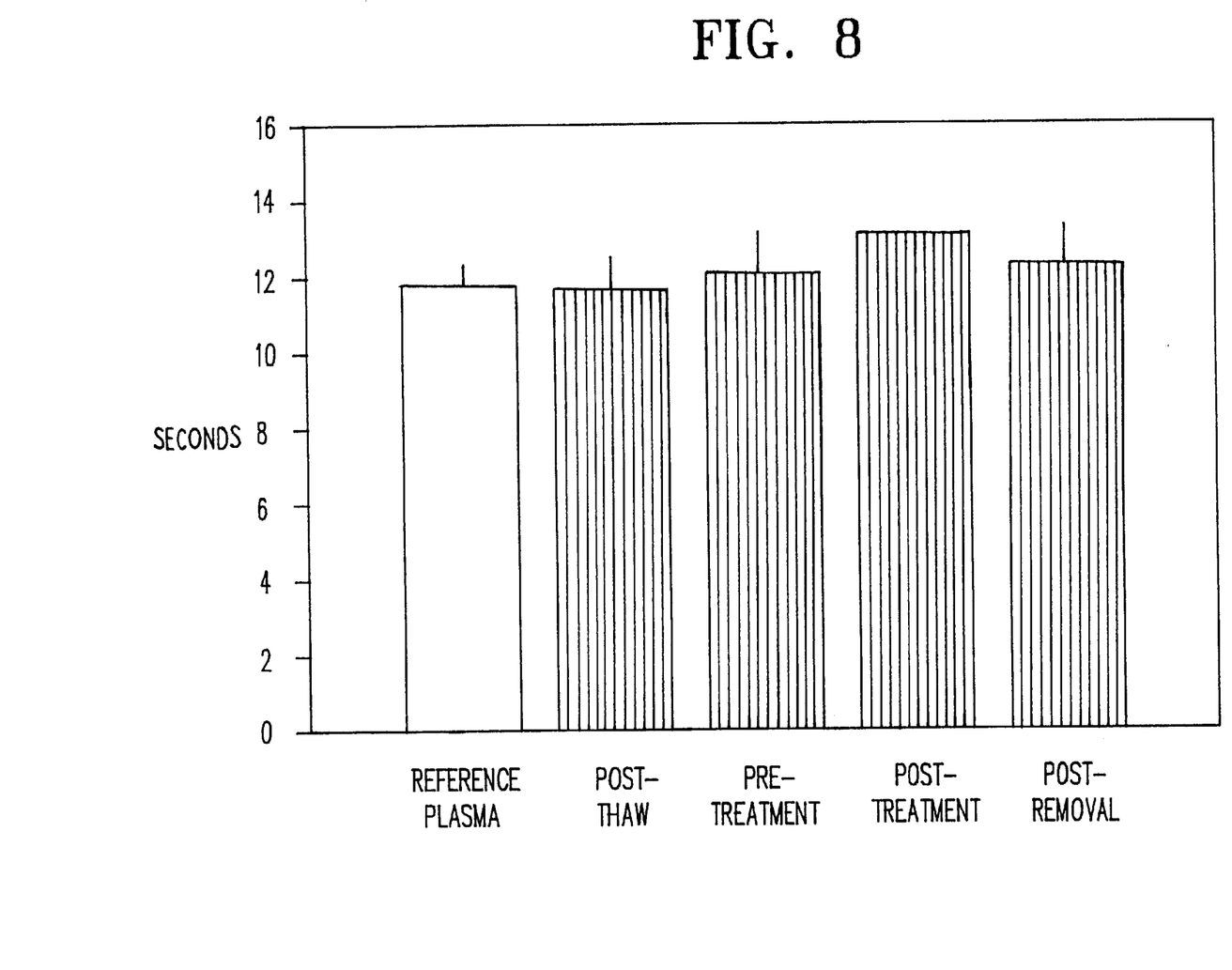
FIG. 8 illustrates graphically results of Example No. 3 and specifically, the content of prothrombin in reference plasma, post-thaw, pretreatment, post treatment, and post removal.
Figure 9:
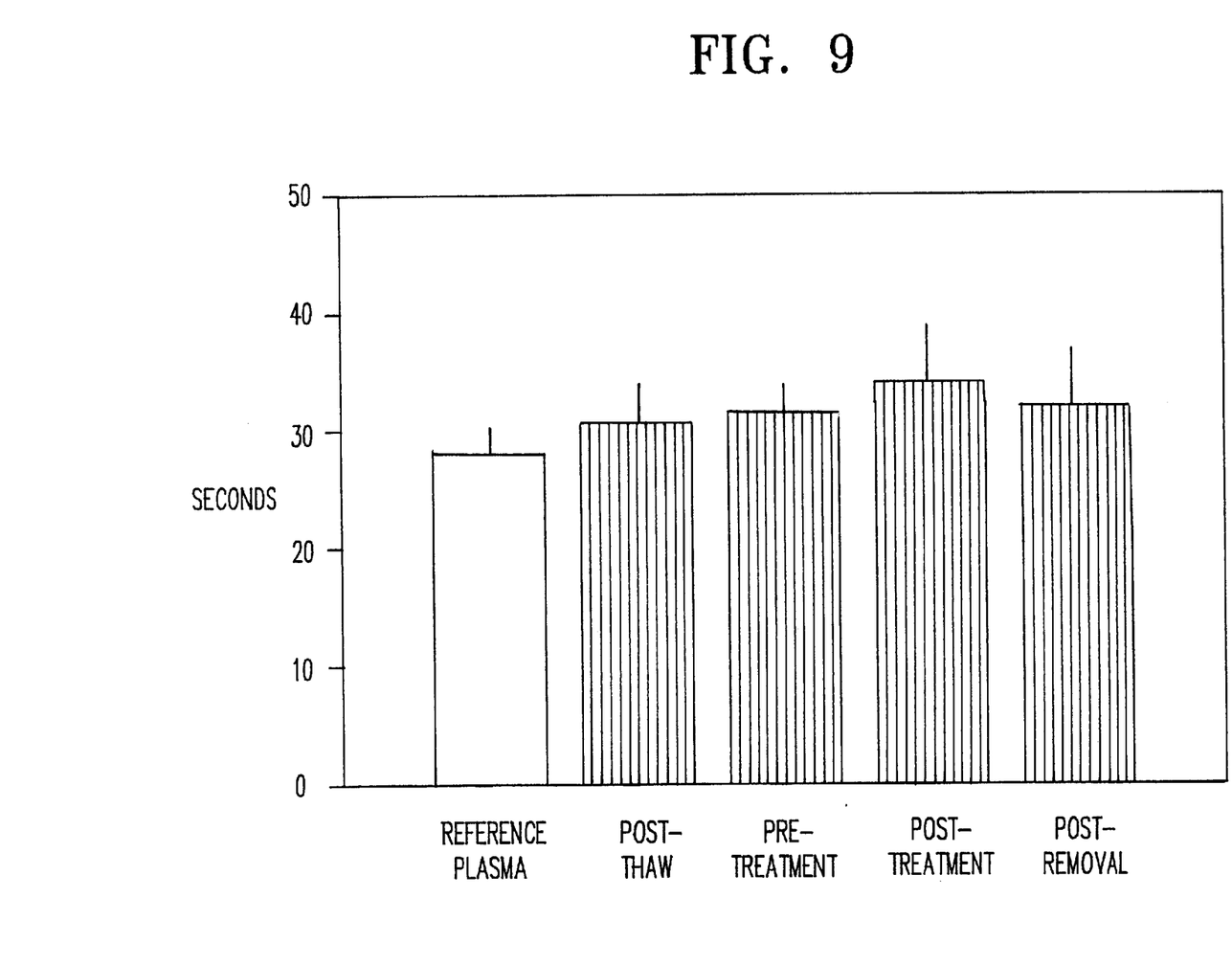
FIG. 9 illustrates graphically results of Example No. 3 and specifically, the content of activated partial thromoplastin time in reference plasma, post-thaw, pretreatment, post treatment, and post removal.

Pursuant to the present invention, as illustrated in FIG. 1, a container 10 will be provided including, for example, a blood component 11. The blood component have added thereto a viral inactivation agent 13.

For example, it is known to collect whole blood in a blood pack. Typically, whole blood is then separated into its component parts. After the blood is separated into the respective components, using a system such as the Optipress® system marketed by affiliates of Baxter International, the blood component can be added to the container 10 including the viral inactivation agent. For example, methylene blue can be added to the plasma component. Of course, if desired, whole blood can be treated with a viral inactivation process. Likewise, if desired, a separate container is not required and the viral inactivation agent can be added to the container in which the component is stored.

The container 10 will include a fluid line 12 that will be coupled to a column 14. As used herein, column refers broadly to a chamber or device that includes material that will remove specific compounds or entities. Accordingly, column includes cartridges, containers, and other means for housing such material.

Pursuant to the present invention, the column 14 will include materials having an affinity for the viral inactivation agent and photoproducts generated thereby. The column will include an inlet 16 allowing product to flow into an interior 18 defined by the housing 20. In an embodiment, porous plates (not illustrated) are located at each end 26 and 28, respectively, of the interior 18 of the housing 20. The porous plates allow the body fluid to flow through an affinity matrix located therein. The resultant product then flows out of the cartridge 14 through the outlet 34.

In use, after the container containing the blood product and viral inactivation agent is activated by light of an appropriate wavelength, the resultant product flows through fluid line 12 and into the affinity column 14. The affinity column 14 will remove excess viral inactivation agents, as well as photoproducts. For example, with respect to methylene blue, excess methylene blue will be removed, as well as Azure A and B. The resultant blood product will then flow through fluid line 36 to a container 38. The blood can be stored in the container 38 and then infused into a patient.

To allow selective flow through the fluid line 12, breakable cannulas, as are known in the art, can be provided. Of course, other means for allowing selective flow through the fluid line 12 can be provided.

It should be noted that although in the illustrated embodiment the cartridge 14 is a separate and distinct component from the container 10, a unitary structure can be provided. In this regard, the column can be integral with the container or coupled thereto as an outlet port of the container.

The material used for the matrix in the affinity column 14 can comprise a variety of different materials. For example, charcoal, an ion exchange resin, or biobeads can be used. As used herein, the term "biobeads" refers to neural macroporous polymeric beads with a high surface area for adsorbing organics from aqueous solutions. Biobeads can vary in their hydrophilic and hydrophobic polarities. The range of believed useful properties of biobeads for the present invention is as follows: polarity (non-polar to intermediate polarity); Dipole Moment (0.1 to 3.0); bead size (30 to 2000 $\mu$m); average pore diameter (45 to 300 angstroms); bead surface area (150 to 1,600 sq. meters/gram dry bead). It has been found that biobeads available from Biorad Laboratories, 2000 Alfred Nobel Drive, Hercules, CA 94547 under the name Macro-Prep® t-butyl HIC function satisfactorily to remove methylene blue and methylene blue photoproducts Azure A and B.

By way of example, and not limitation, examples of the present invention will now be given:

EXAMPLE NO. 1

Removal studies were performed on 4'-aminomethyl-4,5', 8-trimethyl psoralen (AMT). Specifically, three studies were performed, two using activated charcoal columns and one using an ion exchange column. The charcoal columns each consisted of 5.3 grams of activated charcoal obtained from a commercial water purification device. The ion exchange column consisted of less than 8.2 grams of Biorad AG 50W-X8 cation exchange resin.

One unit (80 mL) of plasmalyte platelets containing 40 ug/mL of AMT was passed through the first charcoal filter at a rate of about 30 mL/min. This column removed 86% of the AMT as measured by HPLC. Platelet loss going through the column was 6%. Total protein was reduced by 33%. The platelet morphology score dropped from 355 to 315.

A second charcoal column was tested at a flow rate of about 5 mL/min. This column removed "100%" of the AMT as measured by HPLC. Platelet loss was 14%. Total protein increased by 14%. The platelet morphology score was unchanged by the column (200).

It is clear from these data that the activated charcoal can remove significant amounts of the AMT drug. The removal is inversely proportional to flow rate. The charcoal also appears to remove about one third of the plasma protein and 6–7% of the platelets. At the reduced flow rate (higher drug removal) the platelet morphology score dropped appreciably. We did not see any "fines" coming off the charcoal column.

The ion exchange column clearly removed significant amounts of AMT at low flow rate, but not as much as the charcoal. This column did not appear to remove any plasma protein and platelet loss was higher than with the charcoal. The platelets did not appear to be affected by the ion exchange resin.

EXAMPLE NO. 2

In this example, two more AMT removal studies were performed using biobeads, one with 5.5 grams of 100–200 mesh biobeads and the other with 7.5 grams of 20–50 mesh biobeads.

One unit (50–60 mL) of platelets (in lactated ringers) containing about 20 ug/mL of AMT was pumped through each column at a rate of 7 mL/min. Both columns removed all measurable AMT, but the 20–50 mesh column material yielded a "cleaner" HPLC output. The platelet loss for the 100–200 mesh column was 40% and for the 20–50 mesh was 28%. Total protein was reduced by 13% in the 100–200 mesh column and by 32% in the 20–50 mesh. The platelet morphology for the 100–200 mesh column was unchanged passing through the column at 355, and for the 20–50 mesh column the morphology changed from 130 to 115. It should be noted that the unit of platelets used for the 20–50 mesh biobead column had low platelet counts, bad platelet morphology and low protein content. The columns did not appear to shed any "fines", nor did the beads swell.

The biobeads removed AMT as well as the activated charcoal tested in Example No. 1.

EXAMPLE NO. 3

The following method was performed on ten units of fresh frozen plasma, which had been thawed using an Instacool plasma thawer. An approximately 12 ml sample was collected from each unit as an untreated control sample and aliquoted into tubes for testing. The tubes were labeled with the protocol number, the sample letter and untreated. These units were stored frozen (–80° C.±10° C.) until analyzed.

Treated Samples

The following procedure was performed on ten units of fresh frozen plasma, which had been thawed using the Instacool plasma thawer. An approximately 12 ml untreated sample was removed from each unit, aliquoted and stored frozen (–80° C.±10° C.) until testing. Each unit was sterile connected and added to a container containing methylene blue. These units were labeled K–T. Each methylene blue treatment bag (PL732) was wrapped with aluminum foil and placed on a rotator (Scientific Products Multipurpose rotator Model 151) at room temperature and mix end-over-end at 40–60 rpm for 60 minutes. After mixing, the units were kept in aluminum foil and at room temperature prior to irradiation.

An approximately 16 ml pretreatment sample was removed from each unit and divided into a 4 ml aliquot for methylene blue testing. Prior to irradiation of the plasma units, the light output delivered by the irradiation box was measured. The light output was recorded. The methylene blue plasma mixture was irradiated with the LED light source. The LED light source was placed on top of a horizontal rotator at a speed of 60 rpm. All units were irradiated with red light for 8 J/cm$^2$ exposure. The start and stop times were noted.

An approximately 16 ml post treatment sample was removed from each unit and divided into a 4 ml aliquot for methylene blue testing. The remaining plasma in each plasma unit was passed through a methylene blue removal cartridge in the removal set of FIG. 1 with a plasma expresser. The removal cartridge included biobeads obtained from Biorad Laboratories and sold under the name Macro-Prep® t-butyl HIC. An approximately 16 ml post removal sample was aseptically removed from each unit and divided into a 4 ml aliquot for methylene blue testing.

The following data was generated. FIGS. 2–9 graphically illustrate the data.

TABLE 1

Removal of Methylene Blue (MB) in ug/ml With Biobead Column

| Test | Sample | 1 uM = .374 ug/ml untreated | pretreatment | post treatment | post removal |
|---|---|---|---|---|---|
| MB | K | NT | 0.308 | 0.39 | NRQ |
| MB | L | NT | 0.316 | 0.365 | NRQ |
| MB | M | NT | 0.409 | 0.363 | NRQ |
| MB | N | NT | 0.368 | 0.329 | NRQ |
| MB | O | NT | 0.419 | 0.353 | NRQ |
| MB | P | NT | 0.401 | 0.348 | NRQ |
| MB | Q | NT | 0.422 | 0.306 | NRQ |
| MB | R | NT | 0.426 | 0.409 | NRQ |
| MB | S | NT | 0.43 | 0.344 | NRQ |
| MB | T | NT | 0.292 | 0.384 | NRQ |

*NRQ = No recoverable quantity

TABLE 2

Effect of Column Removal of Methylene Blue on Prothrombin Time

| Test | Sample | untreated | pretreatment | post treatment | post removal |
|---|---|---|---|---|---|
| PT | K | 12 | 12 | 12.2 | 13.8 |
| PT | L | 11.9 | 11.8 | 12.4 | 11.9 |
| PT | M | 12.2 | 12.5 | 13.7 | 13.7 |
| PT | N | 11.5 | 11.5 | 11.8 | 11.4 |
| PT | O | 12.2 | 12.1 | 15.1 | 12.1 |
| PT | P | 13.6 | 12.5 | 13.4 | 12.5 |
| PT | Q | 11.7 | 12.1 | 13.8 | 12.1 |
| PT | R | 11.6 | 13.2 | 15.8 | 13.7 |
| PT | S | 11.8 | 12.1 | 13.8 | 13.2 |
| PT | T | 11.7 | 14.2 | 13.1 | 11.8 |
| | AVG | 12.02 | 12.4 | 13.51 | 12.62 |
| | SD | 0.603 | 0.782 | 1.249 | 0.900 |

TABLE 3

Effect of Colum Removal of Methylene Blue on Activated Partial Thromboplastin Time

| Test | Sample | untreated | pretreatment | post treatment | post removal |
|---|---|---|---|---|---|
| APTT | K | 37.1 | 34.2 | 35.9 | 39 |
| APTT | L | 26 | 26.6 | 26.9 | 27.3 |
| APTT | M | 28.6 | 30.4 | 35.7 | 28.4 |
| APTT | N | 31.7 | 31.1 | 32.3 | 29.7 |
| APTT | O | 31.2 | 32.5 | 38.9 | 31.3 |
| APTT | P | 38.9 | 31.8 | 36.3 | 33.6 |
| APTT | Q | 29.4 | 30.4 | 35.9 | 32.2 |
| APTT | R | 29.9 | 34.1 | 45.3 | 36.1 |
| APTT | S | 29.6 | 30.7 | 31.7 | 39.5 |
| APTT | T | 31.9 | 41.2 | 31.1 | 31.8 |
| | AVG | 31.43 | 32.3 | 35 | 32.89 |
| | SD | 3.882 | 3.801 | 4.990 | 4.185 |

TABLE 4

Effect of Column Removal on Factor IX

| Test | Sample | untreated | pretreatment | post treatment | post removal |
|---|---|---|---|---|---|
| Factor IX | K | 117 | 92 | 94 | 96 |
| Factor IX | L | 100 | 87 | 76 | 87 |
| Factor IX | M | 61 | 59 | 60 | 54 |
| Factor IX | N | 79 | 75 | 81 | 69 |
| Factor IX | O | 68 | 75 | 72 | 65 |
| Factor IX | P | 70 | 63 | 45 | 51 |
| Factor IX | Q | 71 | 67 | 64 | 55 |
| Factor IX | R | 72 | 59 | 70 | 68 |
| Factor IX | S | 88 | 88 | 87 | 71 |
| Factor IX | T | 84 | 82 | 76 | 66 |
| | AVG | 81 | 74.7 | 72.5 | 68.2 |
| | SD | 16.964 | 12.338 | 13.986 | 14.227 |

TABLE 5

Effect of Column Removal on Factor XI

| Test | Sample | untreated | pretreatment | post treatment | post removal |
|---|---|---|---|---|---|
| Factor XI | K | 132 | 118 | 122 | 80 |
| Factor XI | L | 121 | 105 | 96 | 76 |
| Factor XI | M | 118 | 94 | 67 | 44 |
| Factor XI | N | 109 | 104 | 96 | 78 |
| Factor XI | O | 132 | 128 | 126 | 68 |
| Factor XI | P | 77 | 69 | 65 | 43 |
| Factor XI | Q | 102 | 103 | 91 | 54 |
| Factor XI | R | 99 | 78 | 88 | 44 |
| Factor XI | S | 106 | 91 | 95 | 36 |
| Factor XI | T | 87 | 78 | 75 | 39 |
| | AVG | 108.3 | 96.8 | 92.1 | 56.2 |
| | SD | 18.087 | 18.564 | 20.431 | 17.492 |

TABLE 6

Effect of Column Removal on Factor VII

| Test | Sample | untreated | pretreatment | post treatment | post removal |
|---|---|---|---|---|---|
| Factor VII | K | 103 | 95 | 92 | 104 |
| Factor VII | L | 129 | 119 | 119 | 116 |
| Factor VII | M | 63 | 57 | 57 | 61 |
| Factor VII | N | 87 | 84 | 82 | 93 |
| Factor VII | O | 89 | 85 | 89 | 90 |
| Factor VII | P | 59 | 63 | 50 | 60 |
| Factor VII | Q | 86 | 70 | 72 | 80 |
| Factor VII | R | 63 | 55 | 55 | 61 |
| Factor VII | S | 74 | 66 | 64 | 99 |
| Factor VII | T | 92 | 90 | 87 | 95 |
| | AVG | 84.5 | 78.4 | 76.7 | 85.9 |
| | SD | 21.324 | 20.001 | 21.250 | 19.723 |

TABLE 7

Effect of Column Removal on Factor VIII:C

| Test | Sample | untreated | pretreatment | post treatment | post removal |
|---|---|---|---|---|---|
| Factor VIII:C | K | 47 | 41 | 41 | 44 |
| Factor VIII:C | L | 89 | 88 | 83 | 87 |
| Factor VIII:C | M | 93 | 81 | 81 | 71 |
| Factor VIII:C | N | 56 | 51 | 46 | 46 |
| Factor VIII:C | O | 104 | 101 | 88 | 85 |
| Factor VIII:C | P | 46 | 36 | 39 | 36 |
| Factor VIII:C | Q | 76 | 70 | 54 | 54 |
| Factor VIII:C | R | 53 | 43 | 46 | 44 |
| Factor VIII:C | 8 | 63 | 55 | 56 | 54 |
| Factor VIII:C | T | 92 | 75 | 62 | 66 |
| | AVG | 71.9 | 64.1 | 59.6 | 58.7 |
| | SD | 21.522 | 22.098 | 18.265 | 17.795 |

TABLE 8

Effect of Column Removal on Fibrinogen

| Test | Sample | untreated | pretreatment | post treatment | post removal |
|---|---|---|---|---|---|
| Fibrinogen | K | 341 | 290 | 276 | 281 |
| Fibrinogen | L | 308 | 285 | 261 | 248 |
| Fibrinogen | M | 250 | 235 | 204 | 185 |
| Fibrinogen | N | 377 | 345 | 318 | 329 |
| Fibrinogen | O | 285 | 273 | 248 | 252 |
| Fibnnogen | P | 200 | 189 | 149 | 137 |
| Fibrinogen | Q | 308 | 284 | 212 | 214 |
| Fibrinogen | R | 273 | 248 | 223 | 235 |
| Fibrinogen | S | 241 | 244 | 196 | 191 |
| Fibrinogen | T | 299 | 266 | 257 | 255 |
|  | AVG | 288.2 | 265.9 | 234.4 | 232.7 |
|  | SD | 50.861 | 41.162 | 47.664 | 53.994 |

TABLE 9

Effect of Column Removal on Factor V

| Test | Sample | untreated | pretreatment | post treatment | post removal |
|---|---|---|---|---|---|
| Factor V | K | 69 | 65 | 58 | 53 |
| Factor V | L | 84 | 80 | 74 | 77 |
| Factor V | M | 77 | 73 | 69 | 62 |
| Factor V | N | 84 | 79 | 74 | 71 |
| Factor V | O | 63 | 58 | 60 | 54 |
| Factor V | P | 74 | 67 | 62 | 53 |
| Factor V | Q | 71 | 63 | 52 | 49 |
| Factor V | R | 77 | 58 | 65 | 63 |
| Factor V | S | 73 | 62 | 59 | 60 |
| Factor V | T | 53 | 47 | 48 | 43 |
|  | AVG | 72.5 | 65.2 | 62.1 | 58.5 |
|  | SD | 9.384 | 10.130 | 8.634 | 10.244 |

TABLE 10

Effect of Column Treatment of Control Samples on Fibrinogen, Factor V and Factor VII

| Sample | Fibrinogen | Factor V | Factor VII |
|---|---|---|---|
| Reference range | 200–400 mg/dl | 50–150% | 65–135% |
| A untreated | 281 | 82 | 95 |
| B untreated | 249 | 114 | 144 |
| C untreated | 202 | 79 | 103 |
| D untreated | 302 | 62 | 76 |
| E untreated | 399 | 87 | 71 |
| F untreated | 233 | 96 | 82 |
| G untreated | 279 | 93 | 87 |
| H untreated | 263 | 58 | 113 |
| I untreated | 299 | 60 | 80 |
| J untreated | 240 | 111 | 98 |
| AVG | 274.7 | 84.2 | 94.9 |
| SD | 53.614 | 20.077 | 21.584 |

TABLE 11

Effect of Column Treatment of Control Samples on Factor VIII:C, Factor IX and Factor XI

| Sample | Factor VIII:C | Factor IX | Factor XI |
|---|---|---|---|
| Reference range | 50–150% | 60–140% | 65–135% |
| A untreated | 69 | 83 | 101 |
| B untreated | 83 | 115 | 107 |
| C untreated | 31 | 86 | 118 |
| D untreated | 62 | 79 | 101 |
| E untreated | 55 | 90 | 118 |
| F untreated | 96 | 97 | 80 |
| G untreated | 62 | 118 | 142 |
| H untreated | 99 | 85 | 130 |
| I untreated | 150 | 94 | 97 |
| J untreated | 83 | 98 | 103 |
| AVG | 79 | 94.5 | 109.7 |
| SD | 32.180 | 13.109 | 17.784 |

TABLE 12

Effect of Column Treatment of Control Samples on Prothrombin and Activated Partial Thromboplastin Time (APTT)

| Sample | Prothrombin Time (sec) | APTT (sec) |
|---|---|---|
| Reference range |  |  |
| A untreated | 12.3 | 30.7 |
| B untreated | 11.6 | 30.8 |
| C untreated | 12 | 31.5 |
| D untreated | 12.1 | 31 |
| E untreated | 11.7 | 28.4 |
| F untreated | 12.4 | 27.1 |
| G untreated | 11.7 | 25.1 |
| H untreated | 12.5 | 28 |
| I untreated | 12.9 | 28.2 |
| J untreated | 11.5 | 26.5 |
| AVG | 12.07 | 28.7 |
| SD | 0.455 | 2.179 |

After flowing through the cartridge less than 4 nanograms/ml of methylene blue and photoproducts were present in the blood. It should be noted that prior to removal, the blood unit contained 400 nanograms/ml methylene blue. By way of example for a 70 Kg man receiving 2 liters of methylene blue treated fresh frozen plasma he would receive, after removal pursuant to the present invention, 114 ng/Kg of methylene blue. This amounts to $\frac{1}{44,000}$ that of normal intravenous clinical dose. This reduced level effectively eliminates any toxicity concerns.

As illustrated in FIGS. 2–9, except for with respect to Factor XI, the removal step does not remove components from the plasma. FIGS. 2–9 illustrate, graphically content of specific components in: reference plasma; post-thaw; pretreatment; post treatment; and post removal. Specifically, FIGS. 2–9 graphically illustrate, content of: Fibrinogen; Factor V; Factor VII; Factor VII:C; Factor IX; Factor XI; prothrombin; and activated partial thromboplastin time, respectively. As illustrated, the method of the present invention can be used without destroying the therapeutic benefits of the blood to be transfused.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for treating a body fluid to at least substantially inactivate viral contaminants that may be present therein comprising the steps of:

providing a therapeutically useful body fluid;

adding to the body fluid a viral inactivation agent selected from the group consisting of porphyrin, psoralen, phthalocyanine, and hypericin in an amount and under conditions effective to at least substantially inactivate any viral contaminants present in the body fluid without destroying the therapeutic benefits of the body fluid; and passing the resultant product through a column including macroporous polymeric beads having an affinity for the viral inactivation agent and photoproducts generated by irradiating the viral inactivation agent with the light to remove all measurable viral inactivation agent and photoproducts, as determined by high pressure liquid chromatography, from the resultant product without destroying the therapeutic benefits of the body fluid to provide a treated body fluid suitable for administration to a patient.

* * * * *